United States Patent
Rinoie et al.

(10) Patent No.: US 7,475,600 B2
(45) Date of Patent: Jan. 13, 2009

(54) METHOD OF AND APPARATUS FOR EVALUATING ELASTIC MEMBER QUALITY

(75) Inventors: Soushi Rinoie, Wako (JP); Daisuke Okonogi, Wako (JP); Masao Utsunomiya, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 134 days.

(21) Appl. No.: 11/492,946

(22) Filed: Jul. 26, 2006

(65) Prior Publication Data
US 2007/0022822 A1 Feb. 1, 2007

(30) Foreign Application Priority Data
Jul. 29, 2005 (JP) ............... 2005-220574

(51) Int. Cl.
*G01N 3/32* (2006.01)
(52) U.S. Cl. ............... 73/818; 73/788; 73/790; 73/812; 356/237.1; 356/237.2
(58) Field of Classification Search ........... 73/760–860; 356/237.1–237.5
See application file for complete search history.

(56) References Cited

U.S. PATENT DOCUMENTS

| | | | |
|---|---|---|---|
| 3,627,991 A * | 12/1971 | Beall ........................ | 235/454 |
| 4,969,350 A * | 11/1990 | Fogal, Sr. .................. | 73/40.7 |
| 5,130,559 A * | 7/1992 | Leifeld et al. ............ | 250/559.11 |
| 5,642,553 A * | 7/1997 | Leifeld ...................... | 19/98 |
| 5,692,267 A * | 12/1997 | Leifeld ...................... | 19/106 R |
| 6,559,937 B2 * | 5/2003 | Tamada et al. ............ | 356/237.2 |
| 6,647,595 B2 * | 11/2003 | Schurenkramer et al. . | 19/106 R |
| 6,848,149 B1 * | 2/2005 | Baechler .................... | 19/65 R |
| 6,858,339 B2 * | 2/2005 | Utsunomiya et al. ..... | 429/34 |
| 7,173,703 B2 * | 2/2007 | Hosel et al. ............... | 356/429 |
| 7,214,440 B2 * | 5/2007 | Utsunomiya et al. ..... | 429/34 |

FOREIGN PATENT DOCUMENTS

JP 2003-166949 A 6/2003

* cited by examiner

*Primary Examiner*—Harshad Patel
*Assistant Examiner*—Freddie Kirkland, III
(74) *Attorney, Agent, or Firm*—Westerman, Hattori, Daniels & Adrian, LLP.

(57) ABSTRACT

A quality evaluating apparatus has an inspection table for placing a first or second metal separator, and a light-permeable plate for applying a predetermined pressure to a ridge of the first or second metal separator to deform the ridge and allowing a deformed state of the ridge to be inspected through the light-permeable plate while the predetermined pressure is being applied to the ridge. The quality evaluating apparatus also has an image capturing mechanism for capturing an image of the deformed state of the elastic member through the light-permeable plate, and a comparing mechanism for comparing the captured image with a preset image to evaluate the quality of the ridge.

6 Claims, 15 Drawing Sheets

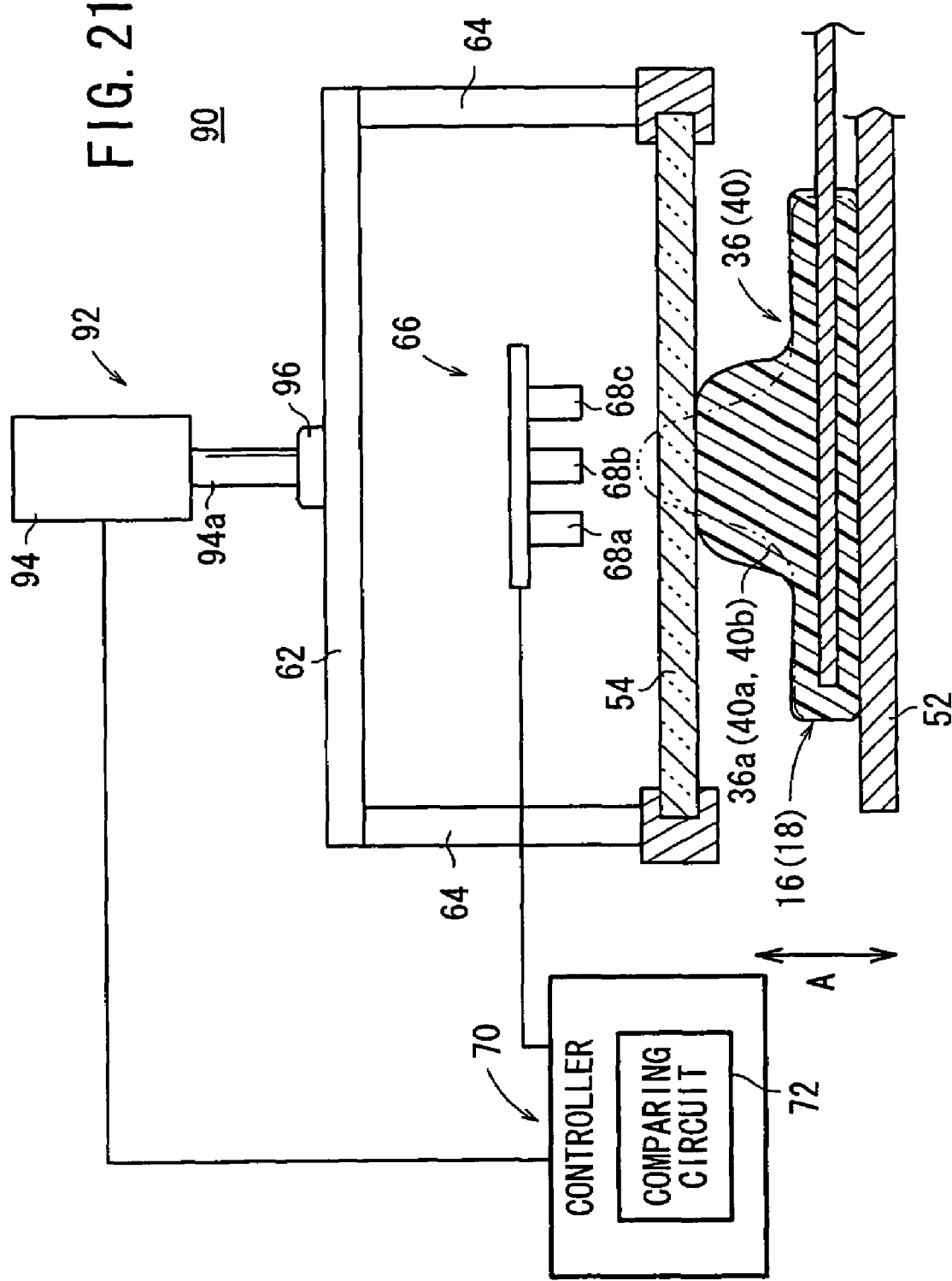

METHOD OF AND APPARATUS FOR EVALUATING ELASTIC MEMBER QUALITY

BACKGROUND OF THE INVENTION

1. Field of the Invention

The present invention relates to a method of and an apparatus for evaluating various quality items, e.g., the shape, flaws, voids, etc., of an elastic member.

2. Description of the Related Art

A solid polymer electrolyte fuel cell employs, for example, a membrane electrode assembly, which comprises an anode electrode, a cathode electrode and an electrolyte membrane interposed between the anode electrode and the cathode electrode. The electrolyte membrane is comprised of a polymer ion exchange membrane. The membrane electrode assembly and separators sandwiching the membrane electrode assembly make up the fuel cell. Each of the anode electrode and the cathode electrode comprises a base made chiefly of carbon and an electrode catalyst layer of precious metal joined to the base.

Each of the separators is comprised of a carbon-based material and sheet metal, and includes a resin seal member (elastic member) for preventing reactive gases and a coolant from leaking out. If the resin seal member has flaws and voids (air bubbles), then it fails to keep a desired sealing capability when the fuel cell is placed under a predetermined tightening load.

Therefore, it is necessary to evaluate the quality of resin seal members for rejecting defective resin seal members. One known quality evaluating apparatus is disclosed as an appearance inspecting apparatus in Japanese Laid-Open Patent Publication No. 2003-166949, for example. The disclosed appearance inspecting apparatus comprises an image capturing unit movable in X and Y directions over the surface of a printed-circuit board or the like that is fixedly placed in a test position, an X-direction illuminating unit mounted on the image capturing unit for illuminating a given area in the X direction, and a Y-direction illuminating unit mounted on the image capturing unit for illuminating a given area in the Y direction. The image capturing unit is stopped at a predetermined position over the surface of the printed-circuit board, and the X-direction illuminating unit and the Y-direction illuminating unit are alternately energized.

When a flaw or defect extending in the Y direction is imaged by the image capturing means, it may not easily be visually confirmed if it is illuminated by only the X-direction illuminating unit. However, the image of the flaw or defect can clearly be seen if it is illuminated by the Y-direction illuminating unit. Conversely, though a flaw or defect extending in the X direction may not easily be visually confirmed if it is illuminated by only the Y-direction illuminating unit, it can clearly be seen if it is illuminated by the X-direction illuminating unit.

According to the conventional appearance inspecting apparatus, however, since the X-direction illuminating unit and the Y-direction illuminating unit are alternately energized and the illuminated flaw or defect is imaged by the image capturing unit, the entire appearance inspecting process is tedious and time-consuming. Though the conventional appearance inspecting apparatus is able to inspect the surface of a printed-circuit board or the like for flaws and defects, it is incapable of detecting voids inside an elastic member, for example. Accordingly, it has heretofore been difficult to detect the quality of elastic members highly accurately.

SUMMARY OF THE INVENTION

It is an object of the present invention to provide a method of and an apparatus for evaluating the quality of an elastic member highly accurately, efficiently, and economically.

According to the present invention, an elastic member is pressed by a light-permeable plate under a predetermined pressure. While the pressure is being applied to the elastic member, a deformed state of the elastic member is inspected through the light-permeable plate to evaluate the quality of the elastic member.

Preferably, an image of the deformed state of the elastic member is captured through the light-permeable plate, and the captured image is compared with a preset image to evaluate the quality of the elastic member.

Further preferably, a plurality of pressing vertical positions for pressing the elastic member are set, and the elastic member is pressed by the light-permeable plate at each of the pressing vertical positions to inspect the deformed state of the elastic member at each of the pressing vertical positions.

Preferably, the elastic member comprises a seal member mounted on a separator of a fuel cell. The seal member is classified according to shape based on the evaluated quality of the seal member, and a plurality of the separators having seal members classified into one group are combined to produce a fuel cell stack comprising a plurality of fuel cells.

According to the present invention, since the pressure is applied to the elastic member by the light-permeable plate, if there is a flaw or defect on the surface of the elastic member, then the flaw or defect is spread and clarified by being pressed by the light-permeable plate. If a void (air bubble) is present inside the elastic member, then when the elastic member is pressed by the light-permeable plate, the width of the elastic member which is held in contact with the light-permeable plate is reduced due to the void. If the elastic member has a different shape, the width of the elastic member which is held in contact with the light-permeable plate varies.

The quality of the elastic member can thus be inspected highly accurately and efficiently through a simple arrangement and process, simply by applying the pressure to the elastic member by the light-permeable plate.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 21 is a schematic view, partly in block form, of an apparatus for evaluating the quality of an elastic member according to the second embodiment of the present invention.

DESCRIPTION OF THE PREFERRED EMBODIMENTS

Figure 1:
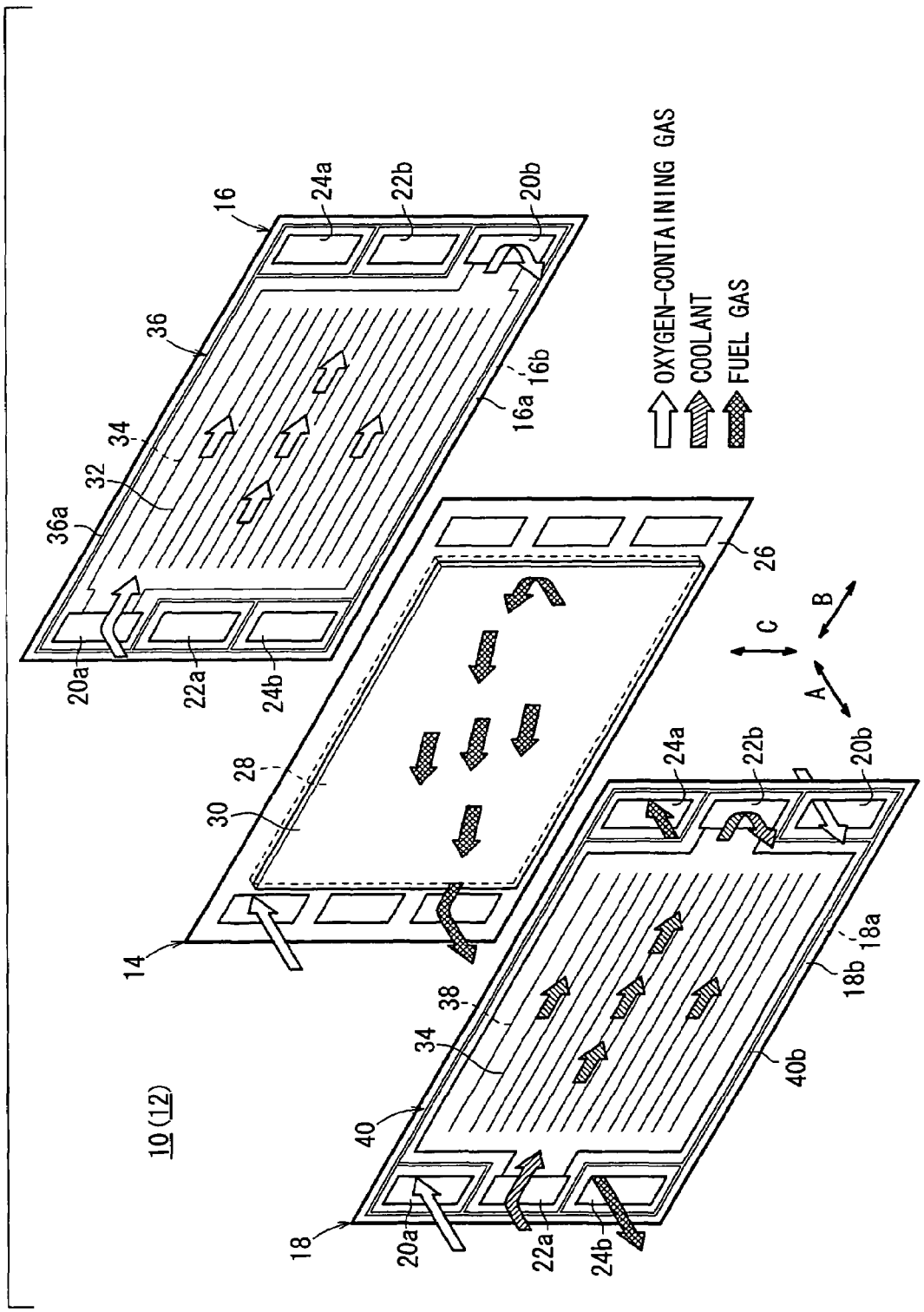
FIG. 1 is an exploded perspective view of a fuel cell to be evaluated by a method of and an apparatus for evaluating the quality of an elastic member according to an embodiment of the present invention.
Figure 2:
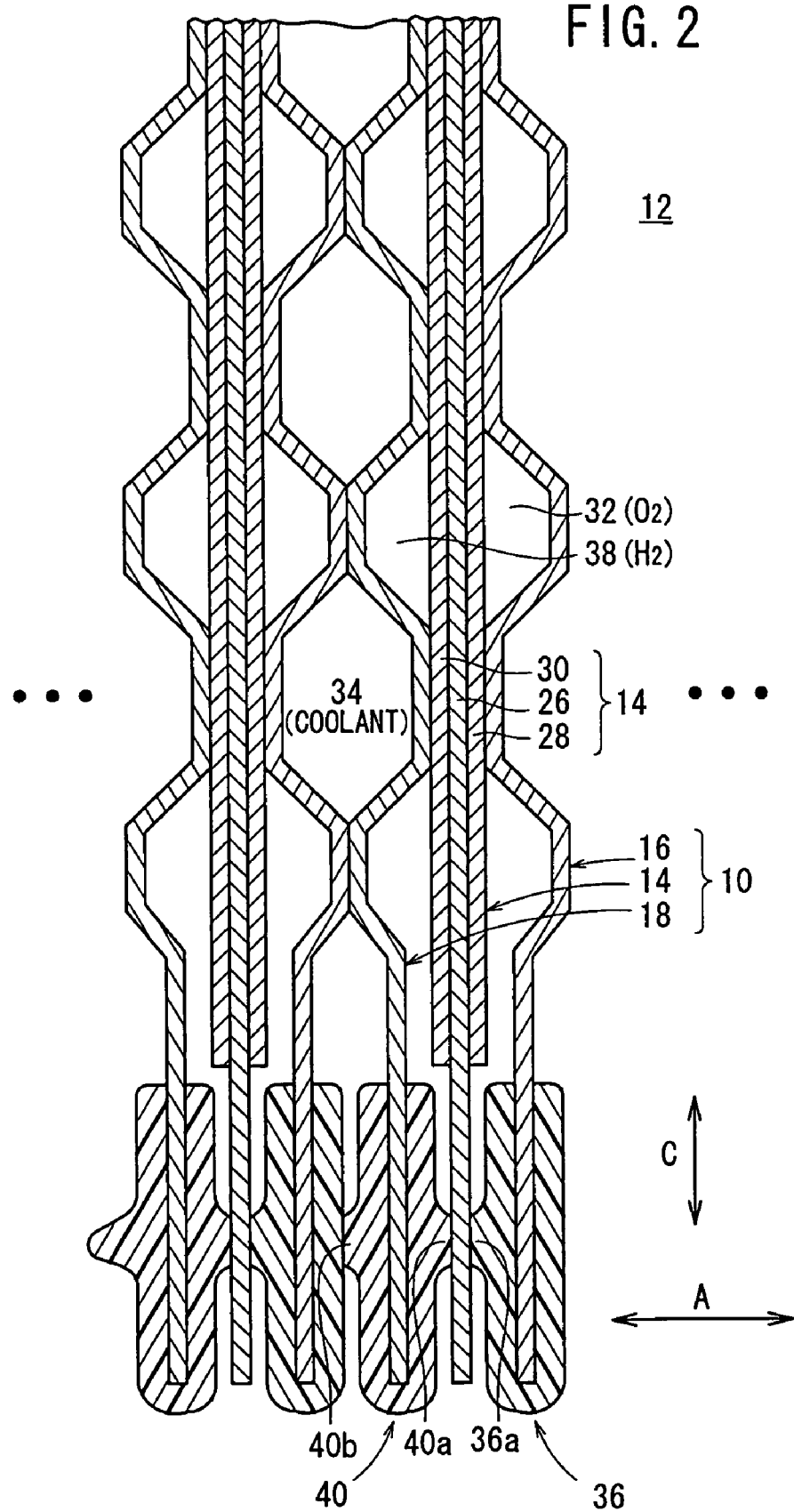
FIG. 2 is a fragmentary cross-sectional view of a fuel cell stack comprising a plurality of fuel cells.

As shown in FIG. 1, a fuel cell 10 to be evaluated by a method of and an apparatus for evaluating the quality of an elastic member according to the present invention, may be used as a single fuel cell. Alternatively, as shown in FIG. 2, a plurality of fuel cells 10 may be stacked into a fuel cell stack 12.

The fuel cell 10 comprises a membrane electrode assembly 14 and first and second metal separators 16, 18 sandwiching the membrane electrode assembly 14 therebetween. Each of the first and second metal separators 16, 18 is made of sheet metal such as a thin metal sheet, e.g., a steel sheet, a stainless steel sheet, an aluminum sheet, a plated steel sheet, or a thin metal sheet whose surface has been treated for corrosion resistance, and is pressed to a desired shape. Each of the first and second metal separators 16, 18 may be replaced with a carbon separator.

The fuel cell 10 has an oxygen-containing gas supply passage 20a for supplying an oxygen-containing gas, a coolant supply passage 22a for supplying a coolant, and a fuel gas discharge passage 24b for discharging a fuel gas such as a hydrogen-containing gas, for example. The oxygen-containing gas supply passage 20a, the coolant supply passage 22a, and the fuel gas discharge passage 24b are defined in one end of the fuel cell 10 in the directions (horizontal directions in FIG. 1) indicated by the arrow B and extend through the membrane electrode assembly 14 and the first and second metal separators 16, 18 in the directions indicated by the arrow A, or in other words, in the direction in which the membrane electrode assembly 14 and the first and second metal separators 16, 18 are stacked. The oxygen-containing gas supply passage 20a, the coolant supply passage 22a, and the fuel gas discharge passage 24b are arrayed in the directions (vertical directions in FIG. 1) indicated by the arrow C.

The fuel cell 10 also has a fuel gas supply passage 24a for supplying the fuel gas, a coolant discharge passage 22b for discharging the coolant, and an oxygen-containing gas discharge passage 20b for discharging the oxygen-containing gas. The fuel gas supply passage 24a, the coolant discharge passage 22b, and the oxygen-containing gas discharge passage 20b are defined in the other end of the fuel cell 10 in the directions indicated by the arrow B and extend through the membrane electrode assembly 14 and the first and second metal separators 16, 18 in the directions indicated by the arrow A. The fuel gas supply passage 24a, the coolant discharge passage 22b, and the oxygen-containing gas discharge passage 20b are arrayed in the directions indicated by the arrow C.

The membrane electrode assembly 14 comprises a solid polymer electrolyte membrane 26 in the form of a thin membrane of perfluorosulfonic acid impregnated with water, and a cathode electrode 28 and an anode electrode 30 sandwiching the solid polymer electrolyte membrane 26 therebetween.

Each of the cathode electrode 28 and the anode electrode 30 comprises a gas diffusion layer made of carbon paper or the like, and an electrode catalyst layer formed by uniformly applying porous carbon particles to the surface of the gas diffusion layer. The porous carbon particles support platinum alloy on their surfaces. The electrode catalyst layers are disposed respectively on the opposite surfaces of the solid polymer electrolyte membrane 26.

An oxygen-containing gas flow field 32 is defined in a surface 16a of the first metal separator 16 which faces the membrane electrode assembly 14, in fluid communication with the oxygen-containing gas supply passage 20a and the oxygen-containing gas discharge passage 20b.

A coolant flow field 34 is defined between a surface 16b of the first metal separator 16 which is opposite to the surface 16a thereof and another second metal separator 18 (see FIG. 2) in fluid communication with the coolant supply passage 22a and the coolant discharge passage 22b. The oxygen-containing gas flow field 32 and the coolant flow field 34 are formed on the respective surfaces 16a, 16b of the first metal separator 16 when the first metal separator 16 is pressed to shape.

A first seal member (elastic member) 36 is formed, by injection-molding, on the surfaces 16a, 16b of the first metal separator 16 around the outer peripheral end of the first metal separator 16. The first seal member 36 may be made of a sealing material, a cushion material, or a packing material of EPDM, NBR, fluororubber, silicone rubber, fluorosilicone rubber, butyl rubber, natural rubber, styrene rubber, chloroprene, acrylic rubber, or the like. The first seal member 36 has a flat seal section and a ridge 36a integral with the flat seal section on the surface 16a (see FIGS. 1 and 2). The ridge 36a serves to hold the oxygen-containing gas flow field 32 in fluid communication with the oxygen-containing gas supply passage 20a and the oxygen-containing gas discharge passage 20b.

Figure 3:
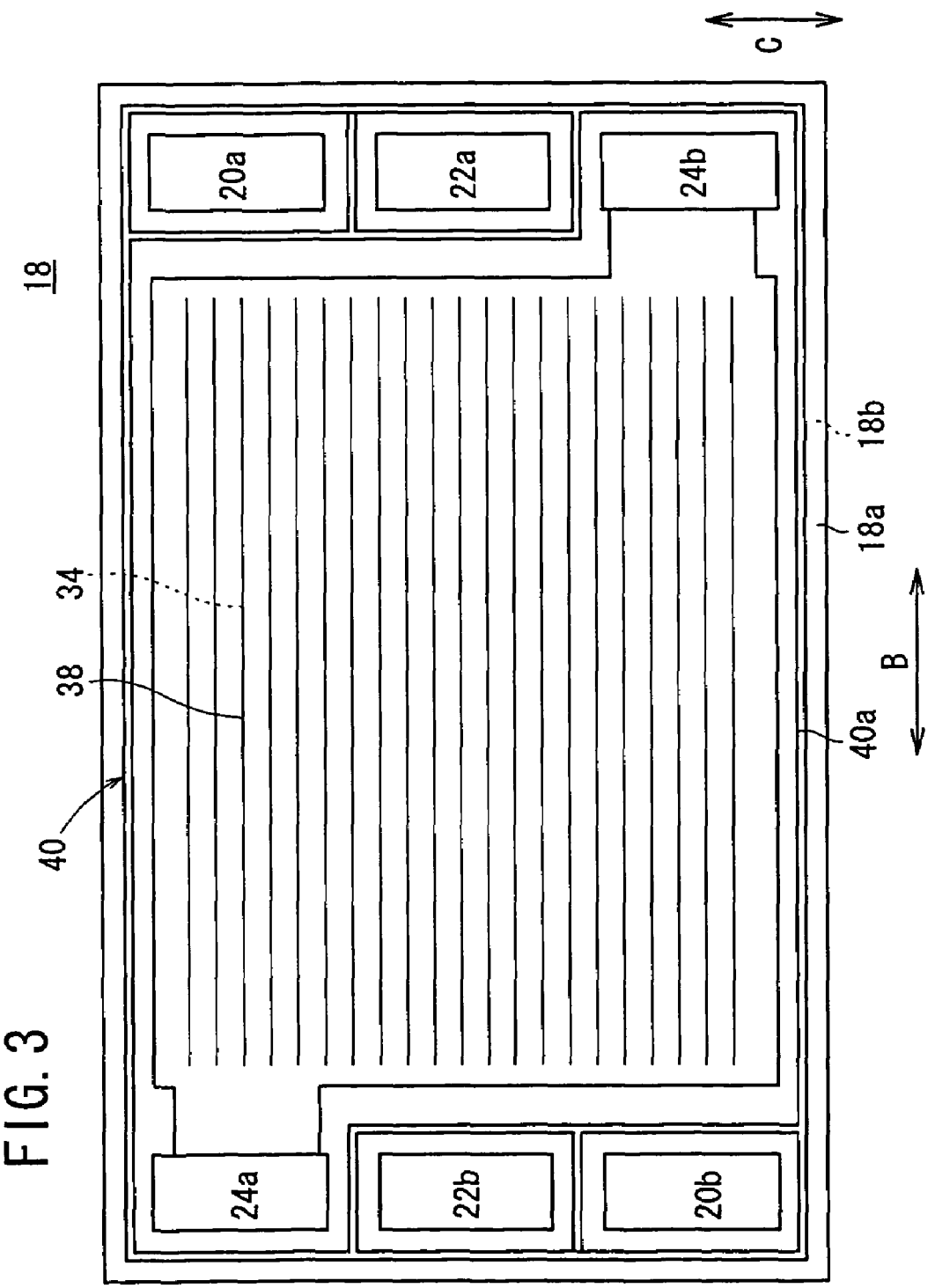
FIG. 3 is a front elevational view of a first metal separator of the fuel cell.

As shown in FIG. 3, a fuel gas flow field 38 is defined in a surface 18a of the second metal separator 18 which faces the membrane electrode assembly 14, in fluid communication with the fuel gas supply passage 24a and the fuel gas discharge passage 24b.

As shown in FIG. 1, a coolant flow field 34 is defined between a surface 18b of the second metal separator 18 which is opposite to the surface 18a thereof and another first metal separator 16 (see FIG. 2) in fluid communication with the coolant supply passage 22a and the coolant discharge passage 22b. The fuel gas flow field 38 and the coolant flow field 34 are formed on the respective surfaces 18a, 18b of the second metal separator 18 when the second metal separator 18 is pressed to shape.

A second seal member (elastic member) 40 is formed, by injection-molding, on the surfaces 18a, 18b of the second metal separator 18 around the outer peripheral end of the second metal separator 18. The second seal member 40 is made of the same material as the first seal member 36.

As shown in FIG. 3, the second seal member 40 has a flat seal section and a ridge 40a integral with the flat seal section on the surface 18a. The ridge 40a serves to hold the fuel gas flow field 38 in fluid communication with the fuel gas supply passage 24a and the fuel gas discharge passage 24b. As shown in FIG. 1, the second seal member 40 also has a flat seal section and a ridge 40b integral with the flat seal section on the surface 18b. The ridge 40b serves to hold the coolant flow field 34 in fluid communication with the coolant supply passage 22a and the coolant discharge passage 22b.

Figure 4:
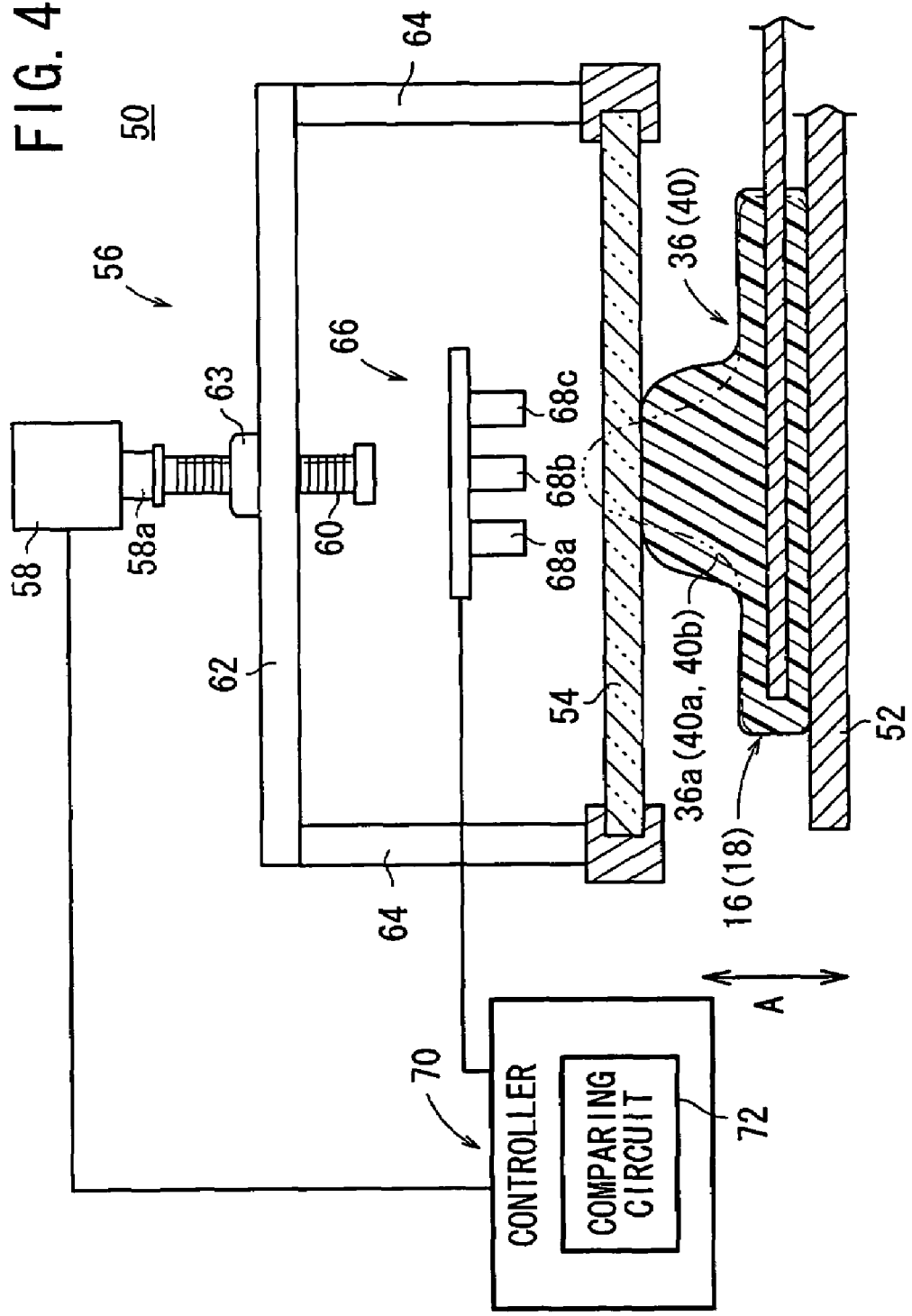
FIG. 4 is a schematic view, partly in block form, of an apparatus for evaluating the quality of an elastic member according to a first embodiment of the present invention.

FIG. 4 shows, partly in block form, an apparatus 50 for evaluating the quality of an elastic member according to a first embodiment of the present invention.

As shown in FIG. 4, the quality evaluating apparatus 50 comprises an inspection table 52 for placing thereon at least one of the first seal member 36 on the first metal separator 16 and the second seal member 40 on the second metal separator 18 (primarily the first seal member 36 in the first embodiment), and a light-permeable plate 54 for pressing the first seal member 36 (or the second seal member 40) to deform the first seal member 36 (or the second seal member 40) under a certain pressure and allowing a deformed state of the first seal member 36 (or the second seal member 40) to be examined while the first seal member 36 (or the second seal member 40) is being kept under the pressure.

The light-permeable plate 54 comprises a glass plate, for example, and is vertically movable in the directions indicated by the arrow A by a moving mechanism 56. The moving mechanism 56 has an actuator such as a motor 58, for example, having an output shaft 58a connected coaxially to a ball screw 60.

The ball screw 60 extends vertically and is screwed in a nut 63 mounted on a vertically movable frame 62. The light-permeable plate 54 that lies horizontally is mounted on the lower ends of legs 64 which extend downwardly from the vertically movable frame 62.

An image capturing mechanism 66 for imaging the deformed state of the first seal member 36 (or the second seal member 40) through the light-permeable plate 54 is disposed above the light-permeable plate 54. The image capturing mechanism 66 comprises a plurality of cameras 68a, 68b, 68c, and sends an image captured by the cameras 68a, 68b, 68c to a controller 70.

The controller 70 functions as a comparing circuit (comparing mechanism) 72 for comparing the image captured by the cameras 68a, 68b, 68c with a preset image. The controller 70 is connected to the actuator such as the motor 58 and/or a sensor, not shown. The vertical position of the light-permeable plate 54 as it presses the first seal member 36 (or the second seal member 40) is detected by an encoder (not shown) mounted on the motor 58 and a sensor (not shown) for detecting the height of the vertically movable frame 62, and a signal indicative of the detected vertical position is supplied to the controller 70.

Operation of the quality evaluating apparatus 50 will be described below in relation to the quality evaluating method according to the first embodiment of the present invention with reference to a flowchart shown in FIG. 5.

Figure 5:
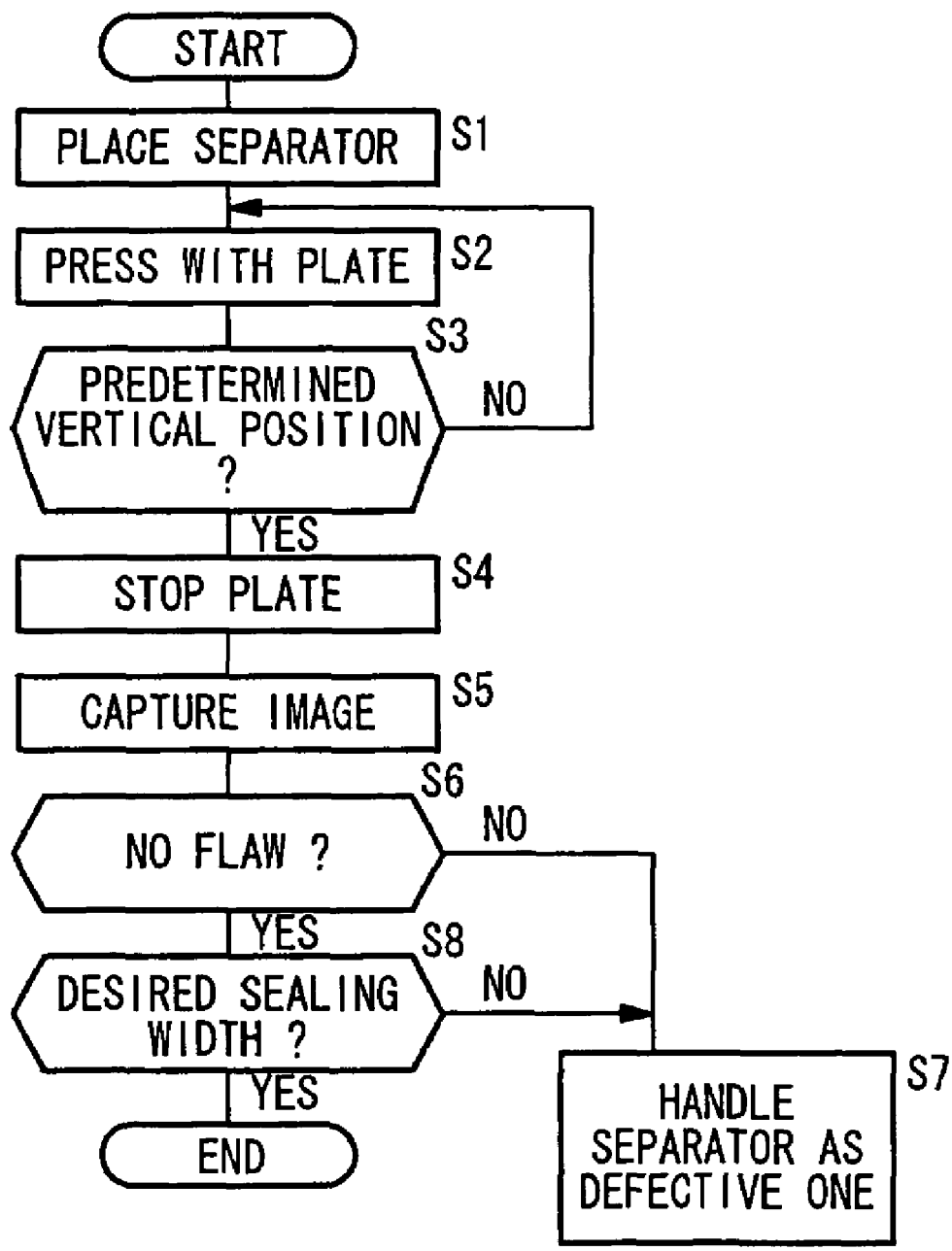
FIG. 5 is a flowchart of a processing sequence of a quality evaluating method according to the first embodiment of the present invention.

As shown in FIG. 4, the first seal member 36 on the first metal separator 16, for example, is placed on the inspection table 52 in step S1 (FIG. 5). A desired area to be inspected of the ridge 36a of the first seal member 36 is positioned below the light-permeable plate 54.

Then, the motor 58 of the moving mechanism 56 is energized to rotate the ball screw 60, lowering the vertically movable frame 62 in unison with the nut 63. The light-permeable plate 54 mounted on the legs 64 of the vertically movable frame 62 is lowered while being kept in a horizontal attitude, and abuts against the ridge 36a of the first seal member 36 in step S2. The light-permeable plate 54 is further lowered to a predetermined pressing vertical position to press the ridge 36a in step S3.

The predetermined pressing vertical position at which the ridge 36a is pressed is set to a position where the same pressure as the tightening load applied to the entire fuel cell stack 12 when in use is applied to the ridge 36a. When the ridge 36a is lowered to the predetermined pressing vertical position (YES in step S3), then control goes to step S4 in which the light-permeable plate 54 is brought to a stop.

Then, the cameras 68a through 68c of the image capturing mechanism 66 capture an image of the deformed state of the ridge 36a through the light-permeable plate 54 in step S5. The captured image is sent to the controller 70, which determines whether there is a flaw on the surface of the ridge 36a or not based on the image in step S6.

Figure 6:
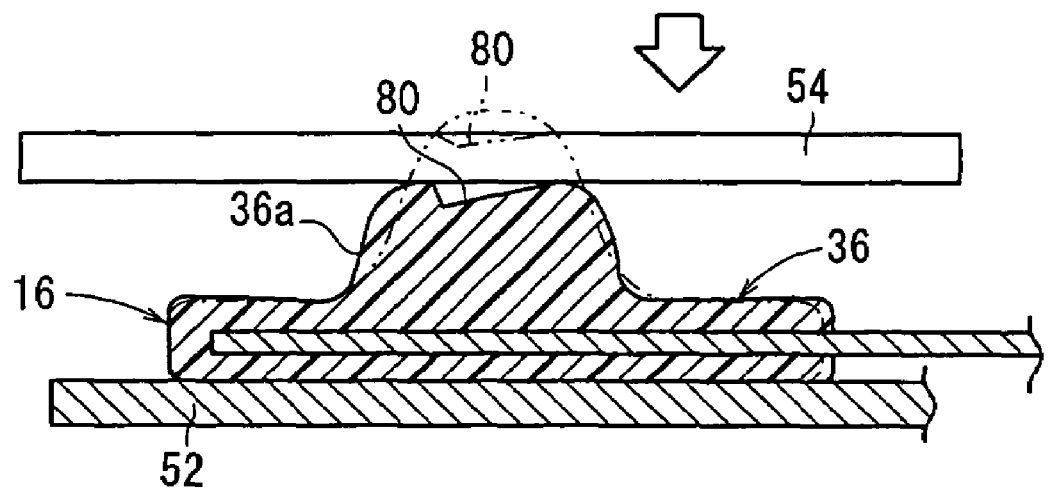
FIG. 6 is a cross-sectional view showing the manner in which a ridge having a flaw on its surface is pressed.
Figure 7:
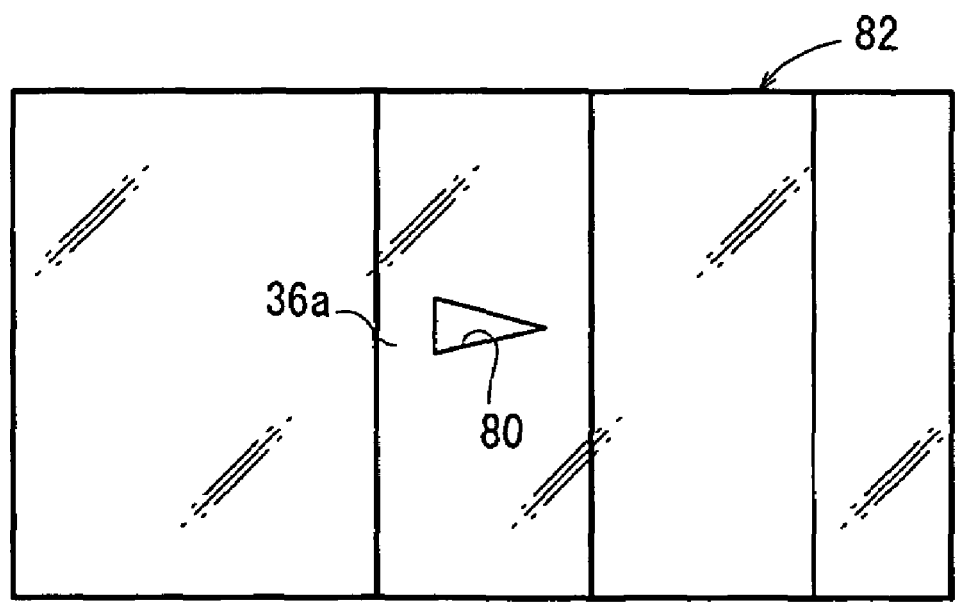
FIG. 7 is a view showing a captured image of the ridge having the flaw on its surface.

If there is a small flaw 80 on the surface of the ridge 36a as shown in FIG. 6, then when the ridge 36a is pressed by the light-permeable plate 54, the flaw 80 is spread and clarified. In the captured image, indicated by 82 in FIG. 7, from the image capturing mechanism 66, the flaw 80 of the ridge 36a is made clearly visible, allowing the viewer to see the flaw 80 reliably.

If it is judged that there is a small flaw 80 on the surface of the ridge 36a (NO in step S6), then control goes to step S7 in which the first metal separator 16 is handled as a defective separator. If it is judged that there is no small flaw 80 on the surface of the ridge 36a (YES in step S6), then control goes to step S8 to determine whether the sealing width of the ridge 36a is a desired sealing width or not. In other words, the controller 70 stores a preset image in advance and the comparing circuit 72 compares the captured image 82 with the preset image.

Figure 8:
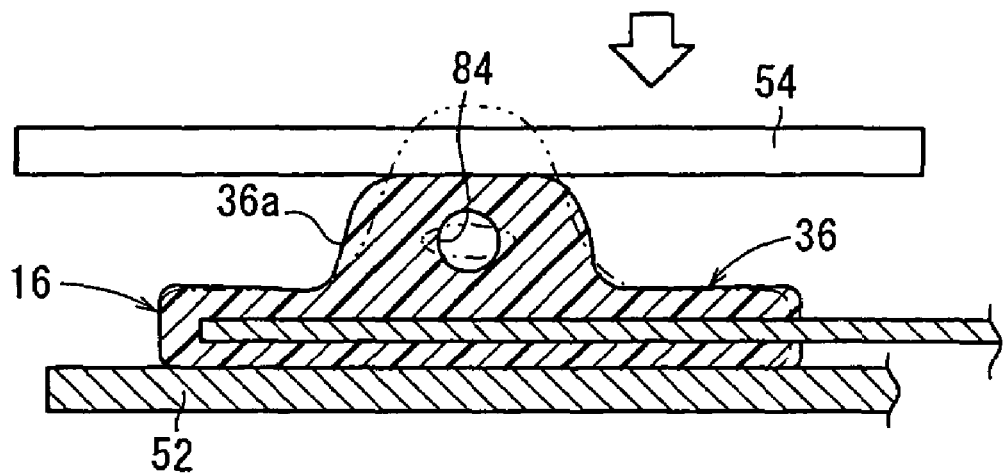
FIG. 8 is a cross-sectional view showing the manner in which a ridge having a void therein is pressed.
Figure 9:
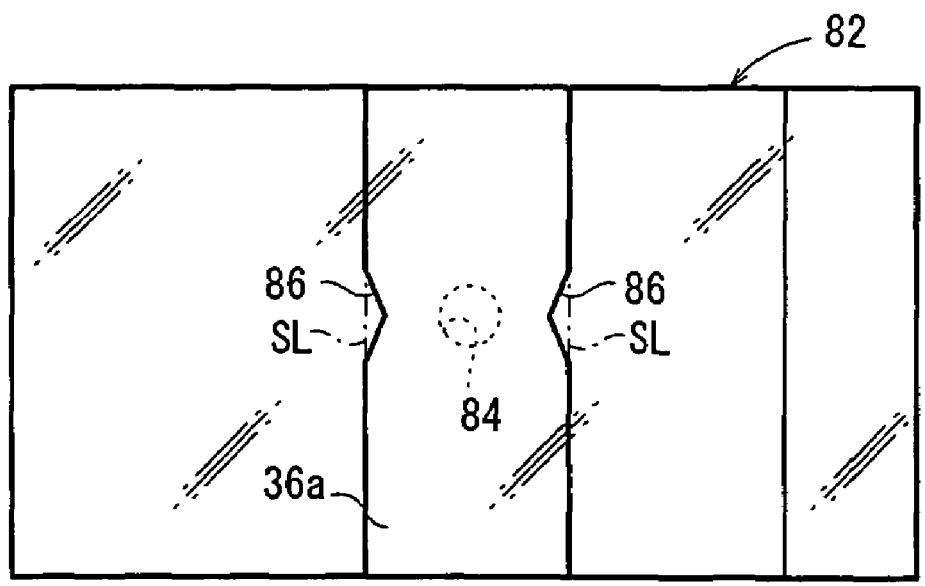
FIG. 9 is a view showing a captured image of the ridge having the void therein.

Specifically, as shown in FIG. 8, if a void (air bubble) 84 is present inside the ridge 36a, then when the ridge 36a is pressed by the light-permeable plate 54, as shown in FIG. 9, constricted regions 86 extending inwardly of prescribed seal lines SL in response to the void 84 are produced in the captured image 82. The controller 70 can detect the void 84 inside the ridge 36a based on the presence of the constricted regions 86 in the captured image 82. The first metal separator 16 having the ridge 36a which includes the void 84 is rejected as a defective component (NO in step S8).

Figure 10:
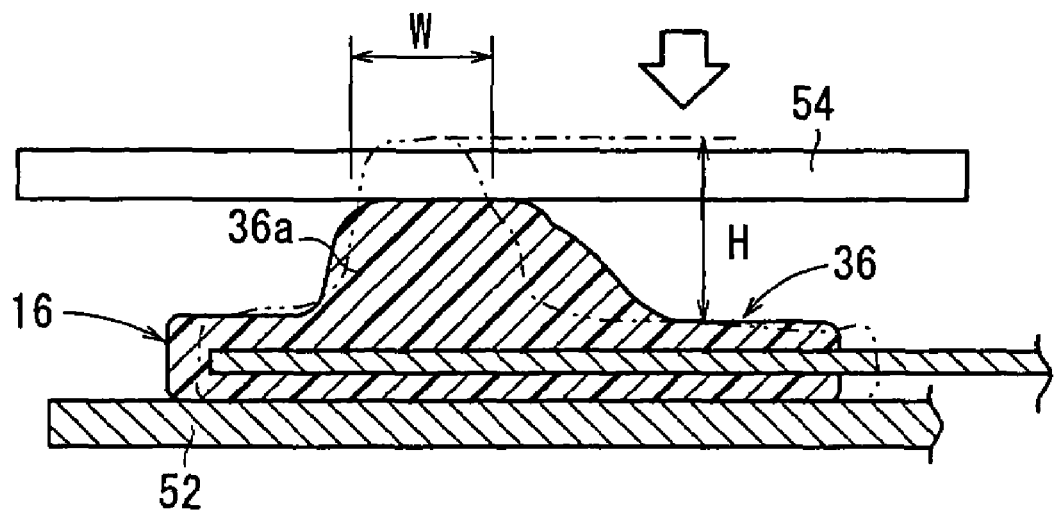
FIG. 10 is a cross-sectional view showing the manner in which a ridge having a shape defect is pressed.
Figure 11:
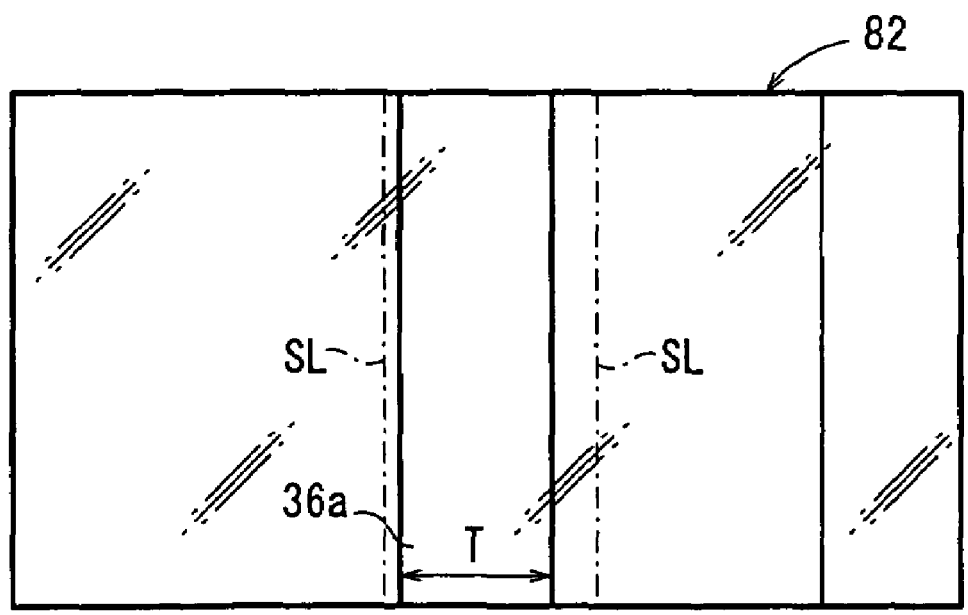
FIG. 11 is a view showing a captured image of the ridge having the shape defect.

If the ridge 36a has a reduced width W and a low height H, as shown in FIG. 10, then when the ridge 36a is pressed by the light-permeable plate 54, as shown in FIG. 11, the ridge 36a is displayed as having a smaller seal width T than the distance between the prescribed seal lines SL, in the captured image 82. The ridge 36a with the reduced width W is judged as suffering a shape defect.

If the sealing width of the ridge 36a is judged as having a desired sealing width (YES in step S8), then other areas of the first seal member 36 are evaluated for quality. If the evaluated quality of all of the desired areas of the first seal member 36 is judged as acceptable, then the first metal separator 16 will be normally used as a component of the fuel cell 10. The ridges 40a, 40b of the second seal member 40 of the second metal separator 18 are also evaluated for quality in the same manner as the ridge 36a of the first seal member 36.

According to the first embodiment, after the first metal separator 16 is placed on the inspection table 52, a pressure is applied to the ridge 36a of the first seal member 36 by the light-permeable plate 54 at a predetermined pressing vertical position, and then the deformed state of the ridge 36a is imaged by the image capturing mechanism 66 through the light-permeable plate 54. Based on the captured image, the flaw 80 on the surface of the ridge 36a and the void 84 inside the ridge 36a can easily and reliably be determined, and the shape defect of the ridge 36a can well be determined.

The quality of the ridge 36a can thus be inspected highly accurately and efficiently, by a simple arrangement and process, simply by applying a pressure to the ridge 36a with the light-permeable plate 54 at a predetermined pressing vertical position.

In the first embodiment, the light-permeable plate 54 is vertically movable by the moving mechanism 56, and the image capturing mechanism 66 is employed. However, the present invention is not limited to this arrangement. Rather than employing the moving mechanism 56 and the image capturing mechanism 66, the operator may manually press the light-permeable plate 54 against the ridge 36a and visually check the deformed state of the ridge 36a through the light-permeable plate 54. Since the flaw 80, the constricted regions 86, and the change in the sealing width are clarified in the captured image, the quality of the ridge 36a can well be evaluated.

Figure 12:
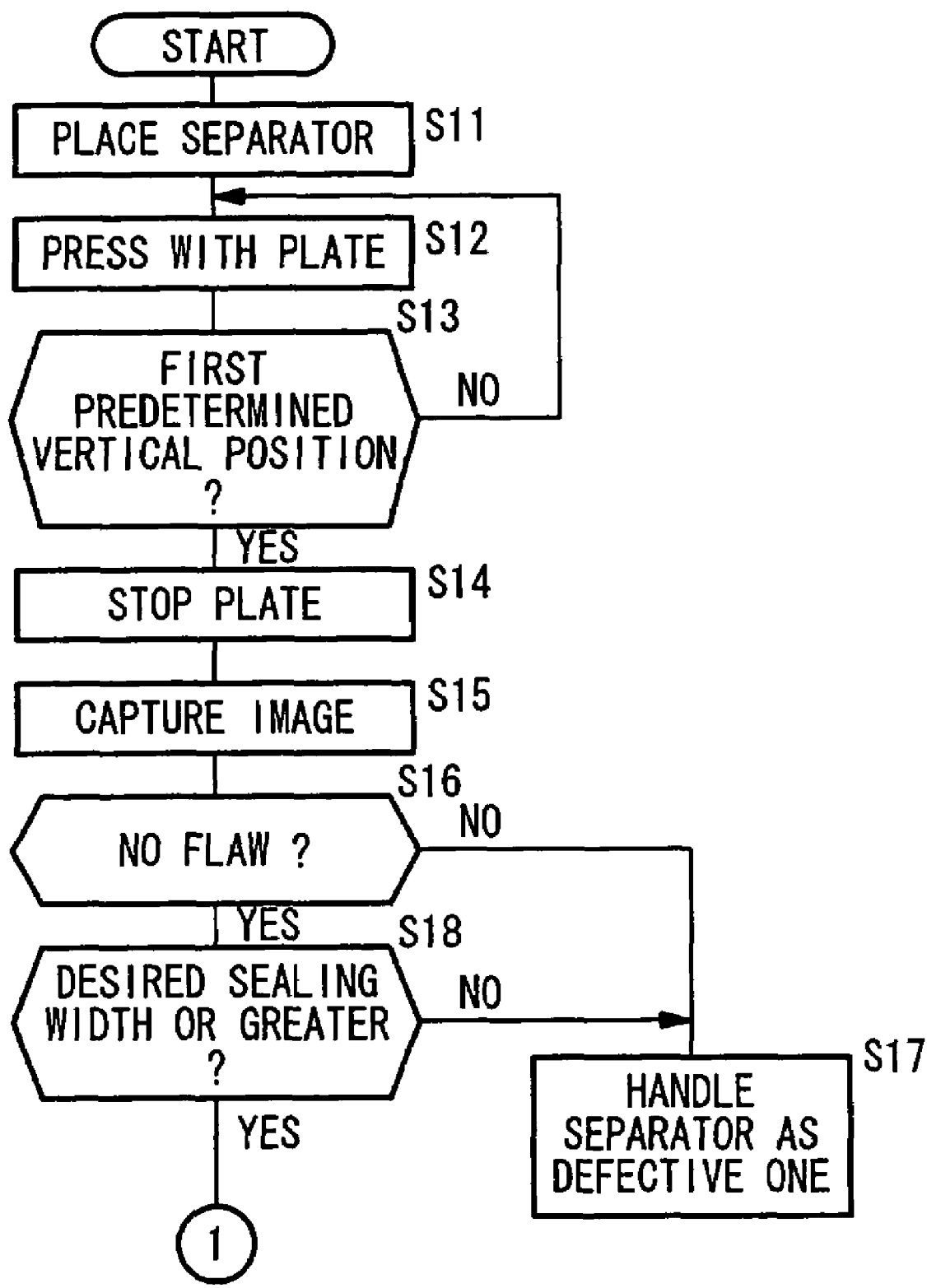
FIGS. 12 and 13 are a flowchart of a processing sequence of a quality evaluating method according to a second embodiment of the present invention.
Figure 13:
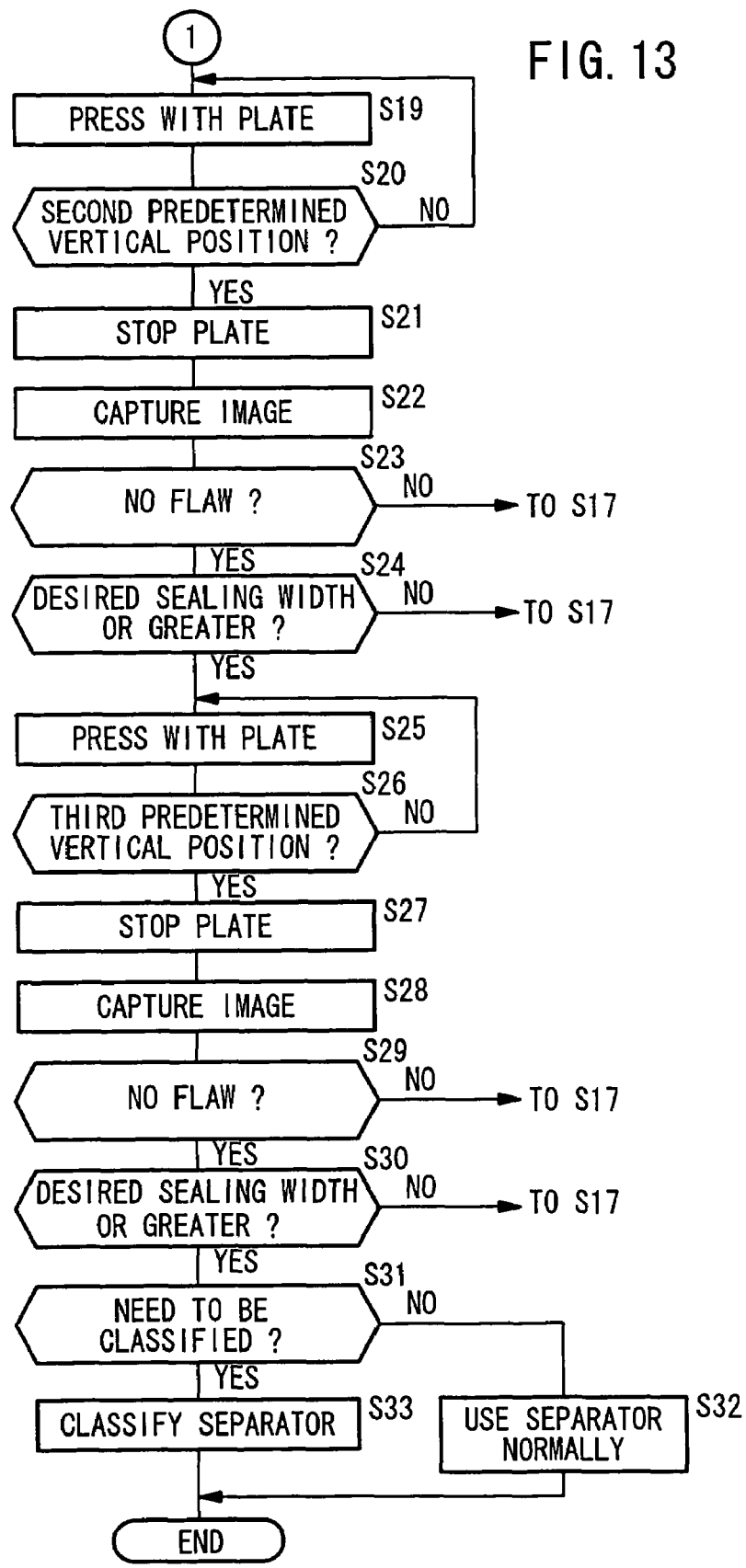

A quality evaluating method according to a second embodiment of the present invention will be described below with reference to a flowchart shown in FIGS. 12 and 13. The quality evaluating method according to the second embodiment is performed by the apparatus 50 shown in FIG. 4. Those details of the quality evaluating method according to the second embodiment which are identical to those of the quality evaluating method according to the first embodiment will be omitted from description. In FIGS. 12 and 13, a first pressing vertical position, a second pressing vertical position, and a third pressing vertical position are related to each other by the relationship: the first pressing vertical position >the second pressing vertical position >the third pressing vertical position, and the second pressing vertical position is a pressing vertical position where the same pressure as the tightening load applied to the entire fuel cell stack 12 when in use is applied to the ridge 36a, and essentially corresponds to the predetermined pressing vertical position according to the first embodiment.

The first metal separator 16 is placed on the inspection table 52, and the light-permeable plate 54 is brought into the first pressing vertical position (where the pressure is of the smallest level) by the moving mechanism 56. Then, the deformed state of the ridge 36a is imaged by the cameras 68a through 68c through the light-permeable plate 54 in steps S11 through S15.

The controller 70 evaluates the quality of the ridge 36a in the first pressing vertical position based on the image captured by the cameras 68a through 68c in steps S16 through S18. Then, the light-permeable plate 54 is lowered to the second pressing vertical position (where the pressure is of an intermediate level) and stopped in the second vertical position in steps S19 through S21. The deformed state of the ridge 36a is imaged by the cameras 68a through 68c through the light-permeable plate 54, and the controller 70 evaluates the quality of the ridge 36a in the second pressing vertical position based on the image captured by the cameras 68a through 68c in steps S22 through S24.

Then, the light-permeable plate 54 is lowered to the third pressing vertical position (where the pressure is of the greatest level) and stopped in the third vertical position, and the deformed state of the ridge 36a is imaged by the cameras 68a through 68c through the light-permeable plate 54 in steps S25 through S28. The controller 70 evaluates the quality of the ridge 36a in the third pressing vertical position based on the image captured by the cameras 68a through 68c in steps S29, S30.

Thereafter, control goes to step S31 to determine whether the first metal separator 16 needs to be classified or not. Specifically, at the second pressing vertical position where the same pressure as the tightening load applied to the entire fuel cell stack 12 when in use is applied to the ridge 36a, the ridge 36a has a sealing width in substantially the same range of contact with the light-permeable plate 54, but may have different widths or heights.

Figure 14:
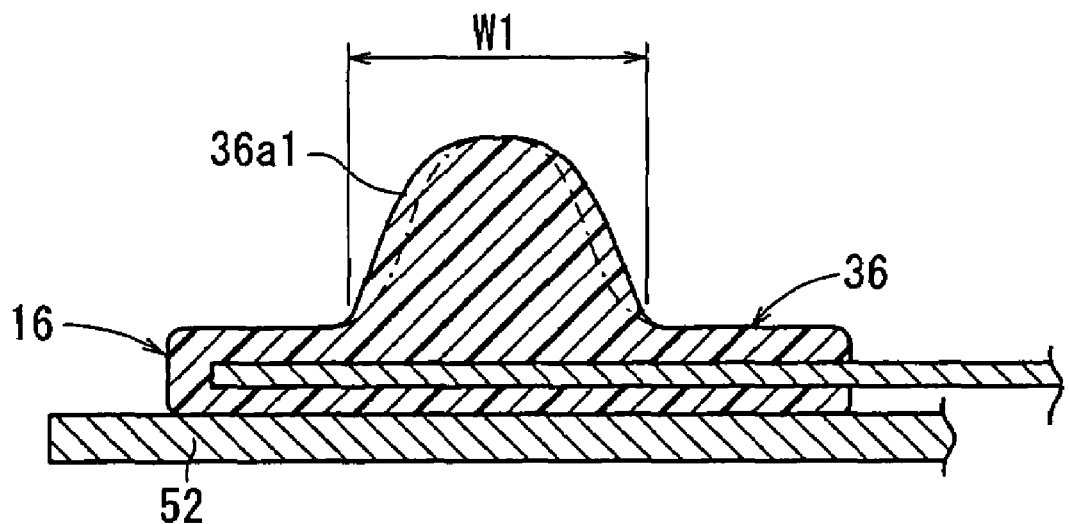
FIG. 14 is a cross-sectional view of a wide ridge.
Figure 15:
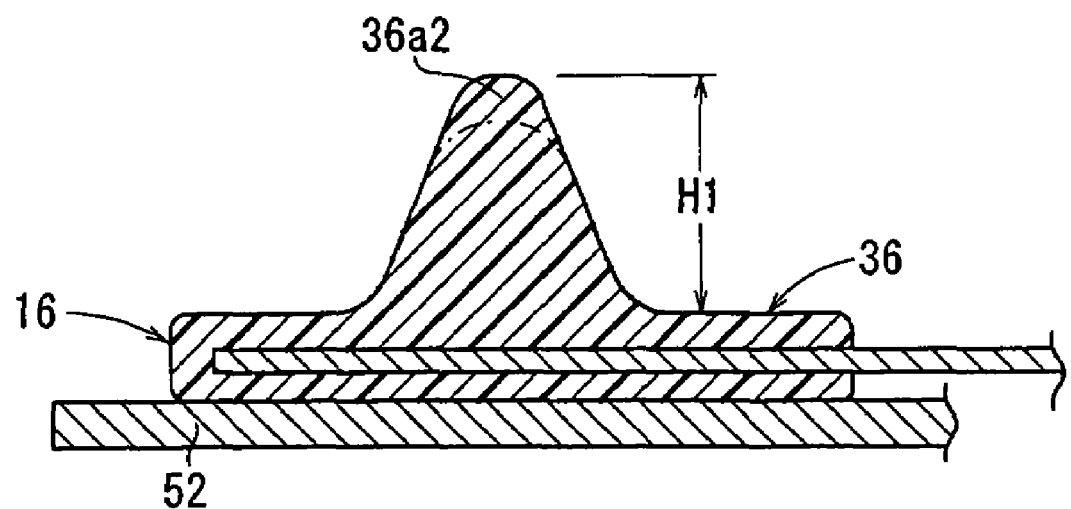
FIG. 15 is a cross-sectional view of a high ridge.
Figure 16:
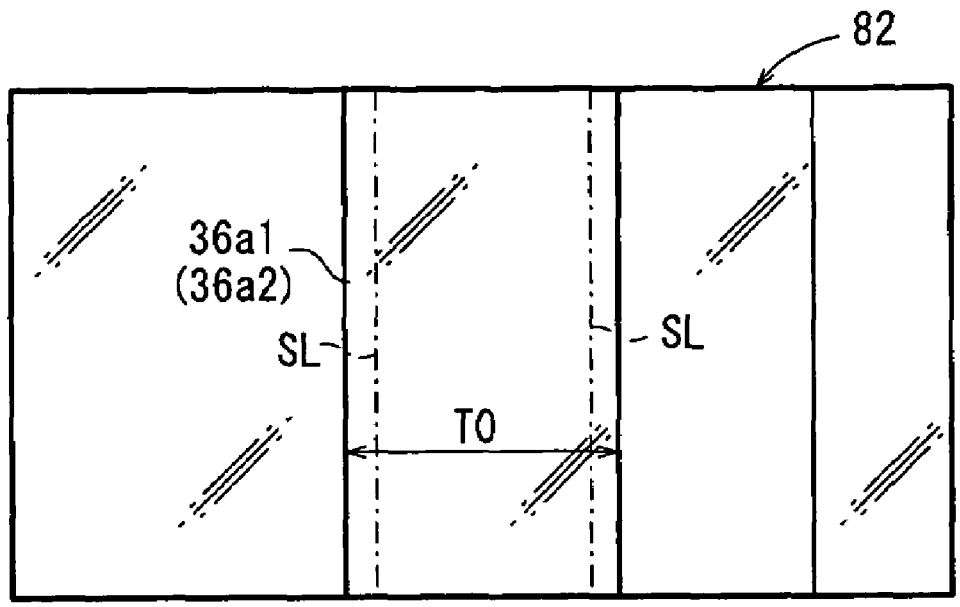
FIG. 16 is a view showing a captured image of the ridge at a second pressing vertical position.

For example, as shown in FIG. 14, a ridge 36a1 has a width W1 greater than a normal profile indicated by the two-dot-and-dash line, and, as shown in FIG. 15, a ridge 36a2 has a height H1 greater than the normal profile indicated by the two-dot-and-dash line. In the captured image 82 taken at the second pressing vertical position, as shown in FIG. 16, the ridges 36a1, 36a2 have a surface of contact with the light-permeable plate 54, providing a sealing width T0 extending outwardly of the prescribed seal lines SL.

Figure 17:
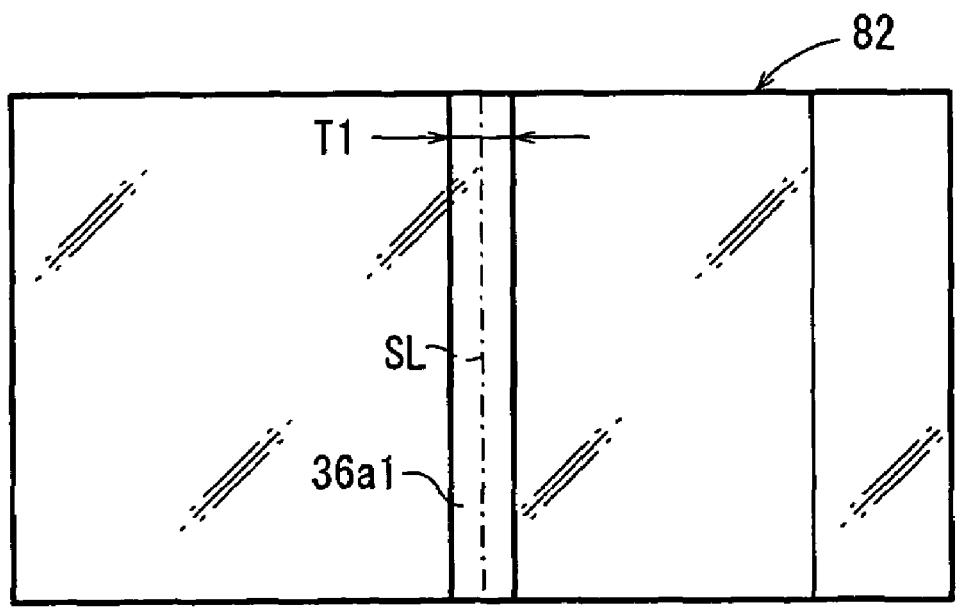
FIG. 17 is a view showing a captured image of the wide ridge at a first pressing vertical position.
Figure 18:
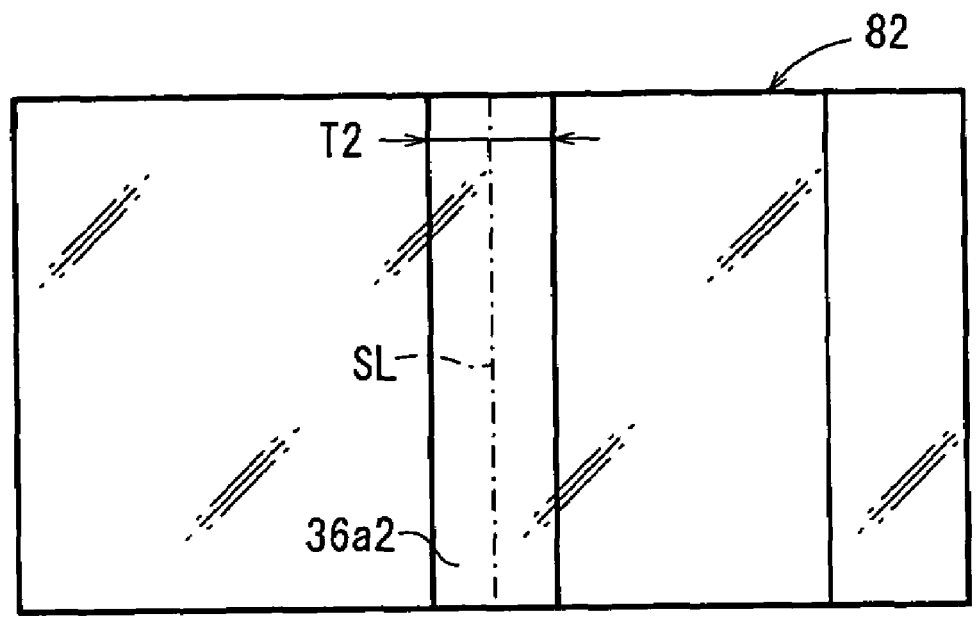
FIG. 18 is a view showing a captured image of the high ridge at the first pressing vertical position.

When the light-permeable plate 54 is brought into the first pressing vertical position, as shown in FIG. 17, the wider ridge 36a1 has a surface of contact with the light-permeable plate 54, providing a sealing width T1 extending across a prescribed seal line SL. At first pressing vertical position, as shown in FIG. 18, the higher ridge 36a2 has a wider surface of contact with the light-permeable plate 54, providing a relatively greater sealing width T2 (>T1).

Figure 19:
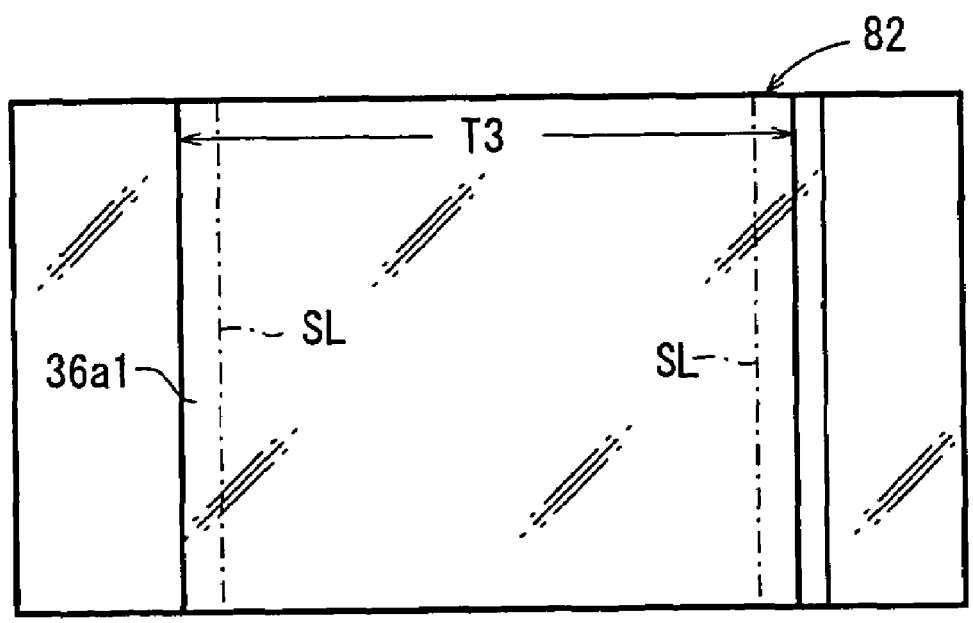
FIG. 19 is a view showing a captured image of the wide ridge at a third pressing vertical position.
Figure 20:
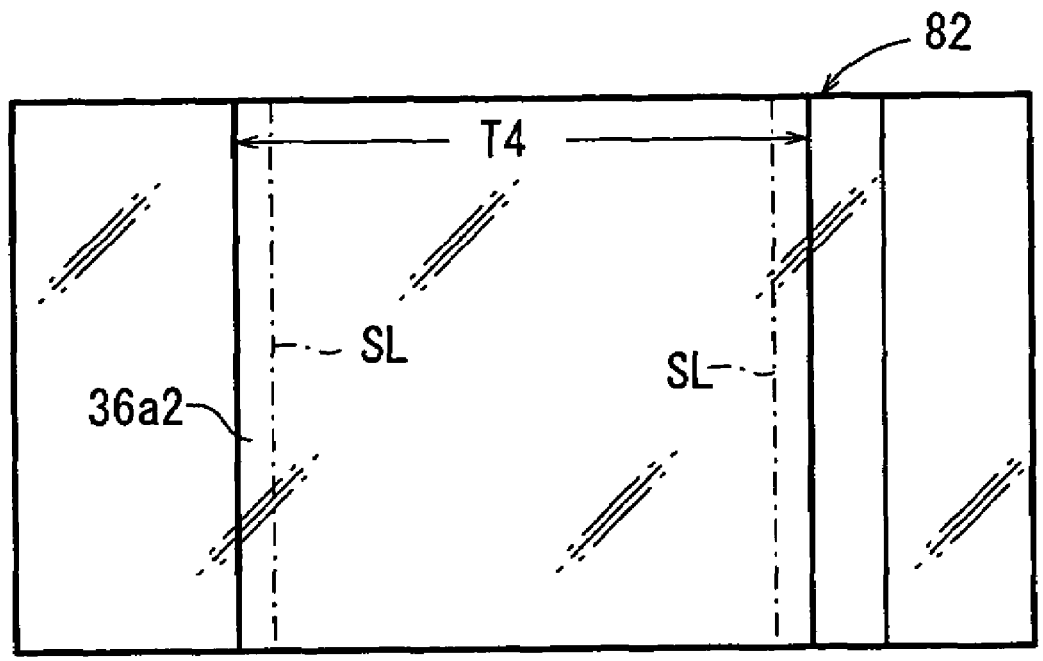
FIG. 20 is a view showing a captured image of the high ridge at the third pressing vertical position.

At the third pressing vertical position, the wider ridge 36a1 has a wider greater sealing width T3 (see FIG. 19), and the higher ridge 36a2 has a relatively smaller surface of contact with the light-permeable plate 54, providing a smaller sealing width T4 (<T3) (see FIG. 20).

Based on the observation of the sealing widths respectively at the first through third pressing vertical positions, the different profiles of the ridges 36a, 36a1, 36a2 can reliably be determined even though the ridges 36a, 36a1, 36a2 are judged as acceptable.

In step S31, the normal ridge 36a is judged as not required to be classified (NO in step S31), and will be used normally in step S32. If the ridge 36a1 or 36a2 is detected, then it is judged as required to be classified (YES in step S31). Control then goes to step S33 in which the ridge 36a1 or 36a2 is classified according to its profile in step S33. Specifically, the wider ridge 36a1 is classified into a wider ridge group, and the higher ridge 36a2 is classified into a higher ridge group.

With a predetermined number of first metal separators 16 having the same profile, a fuel cell is formed, and thus producing a fuel cell stack 12 comprising a plurality of the fuel cells 10. Therefore, each of the fuel cells 10 of the fuel cell stack 12 has its sealing reactive forces kept constant, which would otherwise tend to change due to profile differences, and hence provides a desired sealing capability.

FIG. 21 shows, partly in block form, an apparatus 90 for evaluating the quality of an elastic member according to the second embodiment of the present invention.

Those parts of the apparatus 90 shown in FIG. 21 which are identical to those of the apparatus 50 according to the first embodiment are denoted by identical reference characters, and will not be described in detail below.

The quality evaluating apparatus 90 has a moving mechanism 92 for vertically moving the light-permeable plate 54 in the directions indicated by the arrow A. The moving mechanism 92 has an actuator such as a hydraulic cylinder 94, for example, having a rod 94a that is fixed to the vertically movable frame 62 by a fixing member 96.

The light-permeable plate 54 can be brought into a predetermined pressing vertical position by the hydraulic cylinder 94. Therefore, the quality evaluating apparatus 90 offers the same advantages as the quality evaluating apparatus 50 according to the first embodiment of the present invention.

Although certain preferred embodiments of the present invention have been shown and described in detail, it should be understood that various changes and modifications may be made therein without departing from the scope of the appended claims.

What is claimed is:

1. A method of evaluating the quality of an elastic member, comprising the steps of:
    pressing said elastic member with a predetermined pressure by a light-permeable plate;
    capturing an image of a deformed state of said elastic member through said light-permeable plate while said elastic member is being pressed with said predetermined pressure; and
    comparing the captured image with a preset image to evaluate the quality of said elastic member.

2. A method according to claim 1, further comprising the steps of:
    setting a plurality of pressing vertical positions for pressing said elastic member; and
    pressing said elastic member with said light-permeable plate at each of said pressing vertical positions to inspect the deformed state of said elastic member at each of said pressing vertical positions.

3. A method according to claim 2, wherein said elastic member comprises a seal member mounted on a separator of a fuel cell, further comprising the steps of:
    classifying said seal member according to shape based on the evaluated quality of said seal member; and
    combining a plurality of said separators having seal members classified into one group to produce a fuel cell stack comprising a plurality of fuel cells.

4. A method of evaluating the quality of an elastic member, comprising the steps of:
    pressing said elastic member with a predetermined pressure by a light-permeable plate; and
    inspecting a deformed state of said elastic member through said light-permeable plate while said elastic member is being pressed with said predetermined pressure, thereby evaluating the quality of said elastic member,
    wherein said elastic member comprises a seal member mounted on a separator of a fuel cell.

5. An apparatus for evaluating the quality of an elastic member comprising:
    a light-permeable plate pressing said elastic member with a predetermined pressure to deform said elastic member;
    an image capturing mechanism for capturing an image of a deformed state of said elastic member through said light-permeable plate while said elastic member is being pressed with said predetermined pressure; and
    a comparing mechanism for comparing the captured image with a preset image to evaluate the quality of said elastic member.

6. An apparatus according to claim 5, wherein a plurality of pressing vertical positions for pressing said elastic member with said light-permeable plate are set, further comprising:
    a moving mechanism for moving said light-permeable plate to press said elastic member at each of said pressing vertical positions to inspect the deformed state of said elastic member at each of said pressing vertical positions.

* * * * *